United States Patent [19]

Hamprecht et al.

[11] 4,428,766
[45] Jan. 31, 1984

[54] 2H-1,2,4,6-THIATRIAZINE-1,1-DIOXIDES AND THEIR USE FOR CONTROLLING UNDESIRABLE PLANT GROWTH

[75] Inventors: Gerhard Hamprecht, Winheim; Adolf Parg, Bad Duerkheim; Bruno Wuerzer, Otterstadt, all of Fed. Rep. of Germany

[73] Assignee: BASF Aktiengesellschaft, Fed. Rep. of Germany

[21] Appl. No.: 410,875

[22] Filed: Aug. 24, 1982

[30] Foreign Application Priority Data

Aug. 28, 1981 [DE] Fed. Rep. of Germany ....... 3134145

[51] Int. Cl.³ .................... A01N 43/72; C07D 285/00
[52] U.S. Cl. ............................................. 71/91; 544/7
[58] Field of Search .................................. 544/7; 71/91

[56] References Cited

U.S. PATENT DOCUMENTS

| | | | |
|---|---|---|---|
| 4,013,447 | 3/1977 | Kay | 71/91 |
| 4,316,014 | 2/1982 | Hamprecht | 544/7 |
| 4,343,648 | 9/1982 | Hamprecht et al. | 544/7 |

*Primary Examiner*—John M. Ford
*Attorney, Agent, or Firm*—Keil & Witherspoon

[57] ABSTRACT

2H-1,2,4,6-Thiatriazine-1,1-dioxides of the formula I

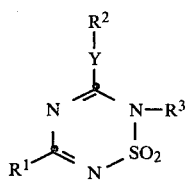

where $R^1$, $R^2$, $R^3$ and Y have the meanings given in the description, are used for controlling undesirable plant growth.

10 Claims, No Drawings

2H-1,2,4,6-THIATRIAZINE-1,1-DIOXIDES AND THEIR USE FOR CONTROLLING UNDESIRABLE PLANT GROWTH

The present invention relates to 2H-1,2,4,6-thiatriazine-1,1-dioxides, herbicides which contain these compounds as active ingredients, and their use for controlling undesirable plant growth.

It has been disclosed that substituted 6H-1,2,4,6-thiatriazin-5-one-1,1-dioxide derivatives have a herbicidal action (German Laid-Open Applications DOS Nos. 2,508,832 and 2,933,889).

We have found that 2H-1,2,4,6-thiatriazine-1,1-dioxides of the formula

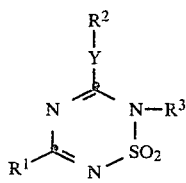

where $R^1$ is hydrogen, a saturated or unsaturated straight-chain or branched aliphatic radical of not more than 10 carbon atoms, a saturated straight-chain or branched aliphatic radical of not more than 10 carbon atoms which is substituted by halogen, alkoxy or alkylmercapto of 1 to 4 carbon atoms, an alkyl or dialkylamino radical where alkyl is of 1 to 6 carbon atoms, cycloalkyl of 3 to 7 carbon atoms, phenyl which is unsubstituted or substituted by halogen, alkyl or alkoxy of 1 to 4 carbon atoms, or benzyl which is unsubstituted or substituted by halogen, $R^2$ is a saturated or unsaturated straight-chain or branched aliphatic radical of not more than 10 carbon atoms, a saturated or unsaturated straight-chain or branched aliphatic radical of not more than 10 carbon atoms which is substituted by halogen, alkoxy or alkylmercapto of 1 to 4 carbon atoms or alkanoyl of 2 to 8 carbon atoms, cycloalkyl of 3 to 7 carbon atoms, alkoxycarbonylalkyl or alkylmercaptocarbonylalkyl where each alkyl is of 1 to 4 carbon atoms, phenyl which is unsubstituted or substituted by halogen, an alkyl, haloalkyl, alkoxy, haloalkoxy, alkylmercapto, haloalkylmercapto, alkylsulfinyl, haloalkylsulfinyl, alkylsulfonyl or haloalkylsulfonyl radical of 1 to 4 carbon atoms, nitro, cyano, azido, carboxyl, thiocyanato, hydroxyiminomethyl, formyl, an alkoxycarbonyl or alkylmercaptocarbonyl radical of 2 to 5 carbon atoms, an N-alkylcarbamyl, N,N-dialkylcarbamyl, N-alkylcarbamylamino or N,N-dialkylcarbamylamino radical where alkyl is of 1 to 4 carbon atoms, 4-alkyl-1,2,4-oxadiazolidine-3,4-dion-2-yl, an alkanoylamino, akoxycarbonylamino or alkylmercaptocarbonylamino radical of 2 to 5 carbon atoms, an N-alkylsulfamyl, N,N-dialkylsulfamyl, N-alkylsulfamylamino or N,N-dialkylsulfamylamino radical where alkyl is of 1 to 4 carbon atoms, alkoxysulfonyl of 1 to 4 carbon atoms, alkoxycarbonylaminosulfonyl of 2 to 5 carbon atoms or an alkoxycarbonylalkoxy, alkylmercaptocarbonylalkoxy, alkoxycarbonylalkylmercapto or alkylmercaptocarbonylalkylmercapto radical where each alkyl is of 1 to 4 carbon atoms, or $R^2$ is benzyl which is unsubstituted or substituted by halogen, nitro or an alkyl, haloalkyl, alkoxy, haloalkoxy or haloalkylmercapto radical of 1 to 4 carbon atoms, or phenoxyalkyl where alkyl is of 2 to 4 carbon atoms, which is unsubstituted or substituted in the phenyl ring by halogen or by alkyl, alkoxy, haloalkyl, haloalkoxy or haloalkylmercapto of 1 to 4 carbon atoms, $R^3$ is hydrogen, a saturated or unsaturated straight-chain or branched aliphatic radical of not more than 10 carbon atoms, or a saturated straight-chain or branched aliphatic radical of not more than 10 carbon atoms which is substituted by halogen or by alkoxy of 1 to 4 carbon atoms, or is cycloalkyl of 3 to 7 carbon atoms, and Y is oxygen, sulfur, —SO— or —SO$_2$—, have a powerful herbicidal action.

In formula I, $R^1$ and $R^3$ are each hydrogen, a saturated or unsaturated straight-chain or branched aliphatic radical of not more than 10 carbon atoms, for example alkyl of not more than 10, preferably not more than 4, carbon atoms, an alkenyl or alkynyl radical of not more than 10, preferably not more than 4, carbon atoms, eg. methyl, ethyl, n-propyl, isopropyl, n-butyl, isobutyl, sec.-butyl, tert.-butyl, n-pentyl, tert.-amyl, n-hexyl, pent-3-yl, 1,2-dimethyl-n-propyl, 1,3-dimethyl-n-butyl, 1-ethyl-2-methyl-n-propyl, 1,2,2-trimethyl-n-propyl, 1,2-dimethyl-4-hexyl, allyl, methallyl, crotyl, 2-ethylhex-2-enyl, hex-5-enyl, 2-methylbut-2-enyl, 2-methylbut-3-enyl, but-1-en-3-yl, 2-methylbut-1-en-4-yl, 2-methylbut-2-en-4-yl, 3-methylbut-1-en-3-yl, propargyl, but-1-yn-3-yl or but-2-ynyl, a saturated straight-chain or branched aliphatic radical of not more than 10, preferably not more than 4, carbon atoms, which is substituted by halogen or alkoxy of 1 to 4 carbon atoms, for example haloalkyl of not more than 10, preferably 1 to 4, carbon atoms or alkyl of not more than 10, preferably not more than 4, carbon atoms which is substituted by alkoxy of 1 to 4 carbon atoms, eg. 2-chloroethyl, 2-chloro-n-propyl, 3-chloro-n-propyl, 2-chloro-sec.-butyl, 2-chloroisobutyl, 2-fluoro-sec.-butyl, 2-fluoroisobutyl, 2-fluoroisopropyl, chloro-tert.-butyl, 2,2,2-trifluoroethyl, 2-methoxyethyl, 2-ethoxyethyl, 3-methoxy-n-propyl, 2-methoxyisopropyl, 3-methoxy-n-butyl, 1-methoxy-sec.-butyl, methoxy-tert.-butyl, ethoxy-tert.-butyl, 2-methoxy-n-butyl or 4-methoxy-n-butyl, or cycloalkyl of 3 to 7 carbon atoms, eg. cyclopropyl, cyclopentyl or cyclohexyl.

$R^1$ is furthermore an alkyl or dialkylamino radical where alkyl is of 1 to 6, preferably 1 to 4, carbon atoms, eg. methylamino, dimethylamino, ethylamino, isopropylamino, n-butylamino, methylethylamino or diisopropylamino, a saturated straight-chain or branched aliphatic radical of not more than 10 carbon atoms which is substituted by alkylmercapto of 1 to 4 carbon atoms, for example alkyl of not more than 10, preferably 1 to 4, carbon atoms which is substituted by alkylmercapto of 1 to 4 carbon atoms, eg. 2-methylmercaptoethyl, 2-ethylmercaptoethyl, 3-methylmercapto-n-propyl, 3-methylmercapto-n-butyl, 1-methylmercapto-sec.-butyl, methylmercapto-tert.-butyl or 2-methylmercapto-n-butyl, or phenyl which is unsubstituted or substituted by halogen, alkyl or alkoxy of 1 to 4 carbon atoms, or benzyl which is unsubstituted or substituted by halogen in the phenyl ring, eg. phenyl, 4-chlorophenyl, 3,4-dichlorophenyl, o-, m- and p-tert.-butylphenyl, o-, m- and p-methoxyphenyl, o-, m- and p-methylphenyl, 4-methoxy-3-chlorophenyl, 2-methyl-4-chlorophenyl, benzyl, 2,6-dichlorobenzyl, 2-chloro-6-fluorobenzyl, 2,6-difluorobenzyl and o-, m- and p-chlorobenzyl.

In formula I, $R^2$ is a saturated or unsaturated straight-chain or branched aliphatic radical of not more than 10 carbon atoms, for example alkyl of not more than 10, preferably not more than 4, carbon atoms, or an alkenyl or alkynyl radical of not more than 10, preferably not more than 4, carbon atoms, eg. methyl, ethyl, n-propyl, isopropyl, n-butyl, isobutyl, sec.-butyl, tert.-butyl, n-pentyl, tert.-amyl, n-hexyl, pent-3-yl, 1,2-dimethyl-n-propyl, 1,3-dimethyl-n-butyl, 1-ethyl-2-methyl-n-propyl, 1,2,2-trimethyl-n-propyl, 1,2-dimethyl-n-hexyl, allyl, methallyl, crotyl, 2-ethylhex-2-enyl, hex-5-enyl, 2-methylbut-2-enyl, 2-methylbut-3-enyl, but-1-en-3-yl, 2-methylbut-1-en-4-yl, 2-methylbut-2-en-4-yl, 3-methylbut-1-en-3-yl, propargyl, but-1-yn-3-yl or but-2-ynyl, a saturated or unsaturated straight-chain or branched aliphatic radical of not more than 10 carbon atoms which is substituted by halogen, alkoxy or akylmercapto of 1 to 4 carbon atoms or alkanoyl of 2 to 8 carbon atoms, for example haloalkyl of not more than 10, preferably not more than 4, carbon atoms, or haloalkenyl or haloalkynyl of not more than 10, preferably not more than 4, carbon atoms, an alkyl, alkenyl or alkynyl radical of not more than 10, preferably not more than 4, carbon atoms, which is substituted by alkoxy or alkylmercapto of 1 to 4 carbon atoms, an alkyl, alkenyl or alkynyl radical of not more than 10, preferably not more than 4, carbon atoms which is substituted by alkanoyl of 2 to 8 carbon atoms, eg. 2-chloroethyl, 2-chloro-n-propyl, 3-chloro-n-propyl, 2-chloroisopropyl, 1-chloromethyl-n-propyl, 2-chloro-sec.-butyl, 2-chloroisobutyl, 2-fluoro-sec.-butyl, 2-fluoroisobutyl, 2-fluoroisopropyl, chloro-tert.-butyl, 2,2,2-trifluoroethyl, 2-methoxyethyl, 2-ethoxyethyl, 3-methoxy-n-propyl, 2-methoxyisopropyl, 3-methoxy-n-butyl, 1-methoxy-sec.-butyl, methoxy-tert.-butyl, ethoxy-tert.-butyl, 2-methoxy-n-butyl, 4-methoxy-n-butyl, 3-chloroprop-1-enyl, 2-chloroprop-1-enyl, 2-chloroprop-2-enyl, 3-chloropropargyl, 4-chlorobut-2-ynyl, 4-chloro-but-1-yn-3-yl, 3-methoxyprop-1-enyl, 2-methoxyprop-1-enyl, 2-methoxyprop-2-enyl, 3-methoxypropargyl, 4-methoxybut-2-ynyl, 4-methoxybut-1-yn-3-yl, 2-methylmercaptoethyl, 2-ethylmercaptoethyl, 3-methylmercapto-n-propyl, 3-methylmercapto-n-butyl, 1-methylmercapto-sec.-butyl, methylmercapto-tert.-butyl, 2-methylmercapto-n-butyl, 3-methylmercaptoprop-1-enyl, 2-methylmercaptoprop-1-enyl, acetylmethyl, propanoylmethyl or butanoylmethyl, or cycloalkyl of 3 to 7 carbon atoms, eg. cyclopropyl, cyclopentyl or cyclohexyl, an alkoxycarbonylalkyl or alkylmercaptocarbonylalkyl radical where each alkyl is of 1 to 4 carbon atoms, eg. 1-ethoxycarbonylethyl or methylmercaptocarbonylmethyl, or phenyl which is unsubstituted or substituted by halogen, an alkyl, haloalkyl, alkoxy, haloalkoxy, alkylmercapto, haloalkylmercapto, alkylsulfinyl, haloalkylsulfinyl, alkylsulfonyl or haloalkylsulfonyl radical of 1 to 4 carbon atoms, nitro, cyano, azido, carboxyl, thiocyanato, hydroxyiminomethyl, formyl, an alkoxycarbonyl or alkylmercaptocarbonyl radical of 2 to 5 carbon atoms, an N-alkylcarbamyl, N,N-dialkylcarbamyl, N-alkylcarbamylamino or N,N-dialkylcarbamylamino radical where alkyl is of 1 to 4 carbon atoms, 4-alkyl-1,2,4-oxadiazolidine-3,5-dion-2-yl, an alkanoylamino, alkoxycarbonylamino or alkylmercaptocarbonylamino radical of 2 to 5 carbon atoms, an N-alkylsulfamyl, N,N-dialkylsulfamyl, N-alkylsulfamylamino or N,N-dialkylsulfamylamino radical where alkyl is of 1 to 4 carbon atoms, alkoxysulfonyl of 1 to 4 carbon atoms, alkoxycarbonylaminosulfonyl of 2 to 5 carbon atoms or an alkoxycarbonylalkoxy, alkylmercaptocarbonylalkoxy, alkoxycarbonylalkylmercapto or alkylmercaptocarbonylalkylmercapto radical where each alkyl is of 1 to 4 carbon atoms, eg. o-, m- and p-trifluoromethylphenyl, o-, m- and p-chlorodifluoromethoxyphenyl, o-, m- and p-trifluoromethoxyphenyl, o-, m- and p-methylmercaptophenyl, o-, m- and p-methylsulfinylphenyl, o-, m- and p-trifluoromethylsulfinylphenyl, o-, m- and p-methylsulfonylphenyl, o-, m- and p-trifluoromethylsulfonylphenyl, o-, m- and p-nitrophenyl, o-, m- and p-cyanophenyl, o-, m- and p-azidophenyl, o-, m- and p-carboxyphenyl, o-, m- and p-thiocyanatophenyl, o-, m- and p-N-hydroxyaminobenzylidene, o-, m- and p-formylphenyl, o-, m- and p-methoxycarbonylphenyl, o-, m- and p-methylmercaptocarbonylphenyl, o-, m- and p-(N-methylcarbamyl)-phenyl, o-, m- and p-(N,N-dimethylcarbamyl)-phenyl, o-, m- and p-acetylaminophenyl, o-, m- and p-methoxycarbonylaminophenyl, o-, m- and p-methylmercaptocarbonylaminophenyl, o-, m- and p-(N-methylsulfamyl)-phenyl, o-, m- and p-(N,N-dimethylsulfamyl)-phenyl, o-, m- and p-(N-methylsulfamylamino)-phenyl, o-, m- and p-(N,N-dimethylsulfamylamino)-phenyl, o-, m- and p-(N-methylcarbamylamino)-phenyl, o-, m- and p-(N,N-dimethylcarbamylamino)-phenyl, o-, m- and p-methoxysulfonylphenyl, o-, m- and p-methoxycarbonylaminosulfonylphenyl, o-, m- and p-methoxycarbonylmethoxyphenyl, o-, m- and p-methoxycarbonylmethylmercaptophenyl, o-, m- and p-(1-methoxycarbonylethoxy)-phenyl, o-, m- and p-(1-methoxycarbonylethylmercapto)-phenyl, o-, m- and p-methylmercaptocarbonylmethoxyphenyl, o-, m- and p-(1-methylmercaptocarbonylethoxy)-phenyl, o-, m- and p-bromophenyl, 2,3-, 2,4-, 2,6- and 3,5-dichlorophenyl, 2,4,5-trichlorophenyl, 3,4-difluorophenyl, 3-chloro-4-fluorophenyl, 3-fluoro-4-chlorophenyl, 3-chloro-4-methoxyphenyl, 3-chloro-4-bromophenyl, 3-chloro-4-methylphenyl, o-, m- and p-isopropylphenyl, o-, m- and p-tert.-butoxyphenyl, 2,4-dinitrophenyl, 2-chloro-4-nitrophenyl, 2,4-dinitro-6-sec.-butylphenyl, 2,6-dibromo-4-cyanophenyl, 2,6-diiodo-4-cyanophenyl, 2,4-dinitro-6-methylphenyl, 3-carboxy-4-nitrophenyl, 2,4-dinitro-6-tert.-butylphenyl, o-, m- and p-(4'-methyl-1',2',4'-oxadiazolidine-3',5'-dion-2-yl)-phenyl, 2,4-dichloro-6-methylphenyl, 2-chloro-4-trifluoromethylphenyl, 3-methoxycarbo-4-nitrophenyl, o-, m- and p-trifluoromethylmercaptophenyl, o-, m- and p-chlorodifluoromethoxyphenyl, or o-, m- and p-chlorodifluoromethylmercaptophenyl, benzyl which is unsubstituted or substituted by halogen, nitro, or an alkyl, haloalkyl, alkoxy, haloalkoxy or haloalkylmercapto radical of 1 to 4 carbon atoms or phenoxyalkyl where alkyl is of 2 to 4 carbon atoms, which is unsubstituted or substituted in the phenyl ring by halogen or by alkyl, alkoxy, haloalkyl, haloalkoxy or haloalkylmercapto of 1 to 4 carbon atoms, eg. 2-methyl-6-chlorobenzyl, o-, m- and p-chlorobenzyl, o-, m- and p-methylbenzyl, o-, m- and p-methoxybenzyl, o-, m- and p-nitrobenzyl, o-, m- and p-trifluoromethylbenzyl, o-, m- and p-trifluoromethoxybenzyl, o-, m- and p-chlorodifluoromethoxybenzyl, o-, m- and p-trifluoromethylmercaptobenzyl, 2-methyl-6-fluorobenzyl, 3,4-dichlorobenzyl, 2-(o-, m- and p-methoxyphenoxy)-ethyl, 2-(o, m- and p-chlorophenoxy)-ethyl, 2-(o-, m- and p-trifluoromethylphenoxy)-ethyl or 2-(o-, m- and p-methylphenoxy)-ethyl.

Preferred compounds of the formula I are those in which $R^1$, $R^2$ and $R^3$ are each alkyl of 1 to 4 carbon atoms and Y is oxygen or sulfur, those in which $R^1$ and $R^3$ are each alkyl of 1 to 4 carbon atoms, $R^2$ is an unsaturated aliphatic radical, for example alkenyl, of 3 or 4 carbon atoms, and Y is oxygen or sulfur, those in which $R'$ and $R^3$ are each alkyl of 1 to 4 carbon atoms, $R^2$ is phenyl which is substituted by halogen, nitro, cyano or alkyl of 1 to 4 carbon atoms and Y is oxygen or sulfur, and those in which $R^1$ and $R^3$ are each alkyl of 1 to 4 carbon atoms, $R^2$ is benzyl which is unsubstituted or substituted by halogen or an alkyl, alkoxy or haloalkoxy radical of 1 to 4 carbon atoms and Y is oxygen or sulfur.

The 2H-1,2,4,6-thiatriazine-1,1-dioxides of the formula I are obtained by reacting a compound of the formula

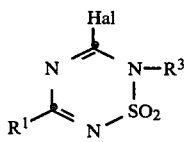
(II)

where $R^1$ and $R^3$ have the above meanings and Hal is halogen, with a compound of the formula

H—Y—$R^2$   (III)

where $R^2$ and Y have the above meanings, or with an alkali metal salt, alkaline earth metal salt or ammonium salt of a compound of the formula III, if necessary in an inert organic solvent, and in the presence or absence of an acid acceptor, at from −50° to +150° C. The reaction may be carried out under atmospheric or superatmospheric pressure, either continuously or batchwise.

If 3-chloro-5-methyl-2-isopropyl-2H-1,2,4,6-thiatriazine-1,1-dioxide and propanol are used as starting materials, the course of the reaction may be represented by the following equation:

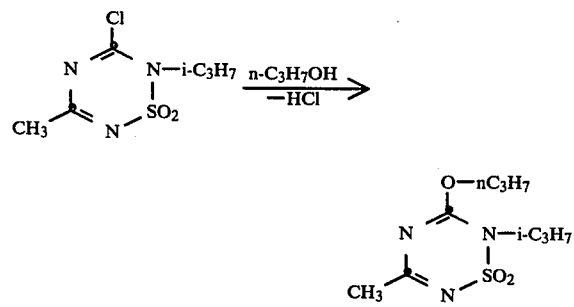

If 3-chloro-5-ethyl-2-isopropyl-2H-1,2,4,6-thiatriazine-1,1-dioxide and sodium 4-chlorobenzenesulfinate are used, the course of the reaction may be represented by the following equation:

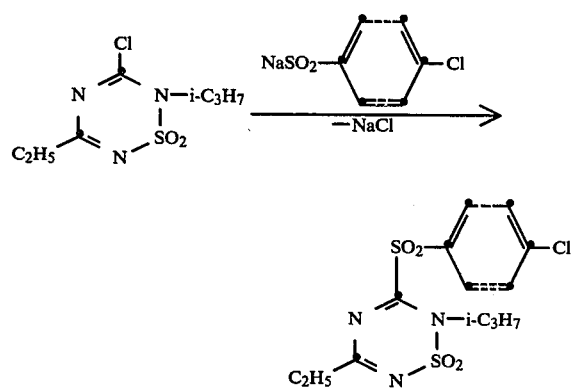

If 3-chloro-5-methyl-2-isopropyl-2H-1,2,4,6-thiatriazine-1,1-dioxide and 2,4-dichlorophenol are used, the course of the reaction may be represented by the following equation:

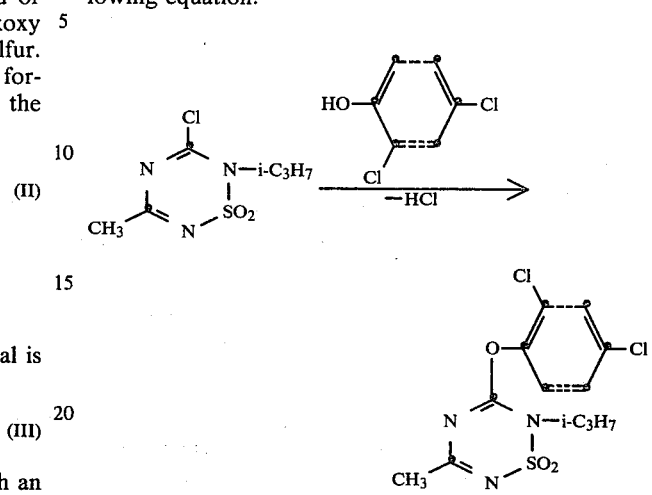

Advantageously, solvents or diluents which are inert under the particular reaction conditions are used for the reaction. Examples of suitable solvents are halohydrocarbons, in particular chlorohydrocarbons, eg. tetrachloroethylene, 1,1,2,2- and 1,1,1,2-tetrachloroethane, dichloropropane, methylene chloride, dichlorobutane, chloroform, chloronaphthalene, dichloronaphthalene, carbon tetrachloride, 1,1,1- and 1,1,2-trichloroethane, trichloroethylene, pentachloroethane, o-, m- and p-difluorobenzene, 1,2-dichloroethane, 1,1-dichloroethane, 1,2-cis-dichloroethylene, chlorobenzene, fluorobenzene, bromobenzene, iodobenzene, o-, m- and p-dichlorobenzene, o-, p- and m-dibromobenzene, o-, m- and p-chlorotoluene and 1,2,4-trichlorobenzene; ethers, eg. ethyl propyl ether, methyl tert.-butyl ether, n-butyl ethyl ether, di-n-butyl ether, di-isobutyl ether, diisoamyl ether, diisopropyl ether, anisole, phenetole, cyclohexyl methyl ether, diethyl ether, ethylene glycol dimethyl ether, tetrahydrofuran, dioxane, thioanisole, and β, β'-dichlorodiethyl ether; nitrohydrocarbons, eg. nitromethane, nitroethane, nitrobenzene, o-, m- and p-chloronitrobenzene and o-nitrotoluene; nitriles, eg. acetonitrile, butyronitrile, isobutyronitrile, benzonitrile and m-chlorobenzonitrile; aliphatic and cycloaliphatic hydrocarbons, eg. heptane, pinane, nonane, o-, m- and p-cymene, gasoline fractions boiling within a range from 70° to 190° C., cyclohexane, methylcyclohexane, decalin, petroleum ether, hexane, naphtha, 2,2,4-trimethylpentane, 2,2,3-trimethylpentane, 2,3,3-trimethylpentane and octane; esters, eg. ethyl acetate, ethyl acetoacetate and isobutyl acetate; amides, eg. formamide, methylformamide and dimethylformamide; and ketones, eg. acetone and methyl ethyl ketone, and, if appropriate, also water, and mixtures of the above. The solvent is advantageously used in an amount of from 100 to 2,000, preferably from 200 to 700, % by weight, based on the starting material II.

The acid acceptors used can be any of the conventional acid-binding agents. These preferably include tertiary amines, alkaline earth metal compounds, ammonium compounds and alkali metal compounds, as well as mixtures of these. However, zinc compounds may also be used. Specific examples of basic compounds which may be used are potassium hydroxide, sodium hydroxide, potassium carbonate, sodium carbonate, lithium hydroxide, lithium carbonate, sodium bicarbonate, potassium bicarbonate, calcium hydroxide, calcium oxide, barium oxide, magnesium hydroxide, magnesium oxide, barium hydroxide, calcium carbonate, magnesium carbonate, magnesium bicarbonate, magnesium acetate, zinc hydroxide, zinc oxide, zinc carbonate, zinc bicarbonate, zinc acetate, sodium formate, sodium acetate, trimethylamine, triethylamine, tripropylamine, triisopropylamine, tributylamine, triisobutylamine, tri-sec.-butylamine, tri-tert.-butylamine, tribenzylamine, tricyclohexylamine, triamylamine, trihexylamine, N,N-dimethylaniline, N,N-diethylaniline, N,N-dipropylaniline, N,N-dimethyltoluidine, N,N-diethyltoluidine, N,N-dipropyltoluidine, N,N-dimethyl-p-aminopyridine, N,N-diethyl-p-aminopyridine, N,N-dipropyl-p-aminopyridine, N-methylpyrrolidone, N-ethylpyrrolidone, N-methylpiperidine, N-ethylpiperidine, N-methylpyrrolidine, N-ethylpyrrolidine, N-methylimidazole, N-ethylimidazole, N-methylpyrrole, N-ethylpyrrole, N-methylmorpholine, N-ethylmorpholine, N-methylhexamethyleneimine, N-ethylhexamethyleneimine, pyridine, quinoline, α-picoline, β-picoline, γ-picoline, isoquinoline, pyrimidine, acridine, N,N,N',N'-tetramethylethylenediamine, N,N,N',N'-tetraethylethylenediamine, quinoxaline, quinazoline, N-propyldiisopropylamine, N,N-dimethylcyclohexylamine, 2,6-lutidine, 2,4-lutidine, trifurfurylamine and triethylenediamine.

The acid acceptors are advantageously used in from 80 to 120% of the amount equivalent to the starting material II. However, the hydrogen halide formed can also be removed by sweeping with an inert gas, for example nitrogen.

The starting materials III required for the reaction are in general employed in from 80 to 120% of the amount equivalent to the starting material II. However, the starting material III may also be employed directly as the solvent. Alternatively, the starting material III can be initially introduced in one of the above diluents, after which the starting material II and an acid acceptor are added, simultaneously or in any desired sequence, through two separate feeds.

An advantageous method of preparing the novel compounds is to take the starting material II, in the presence of absence of one of the above diluents and to add the starting material III and an acid acceptor, simultaneously or successively. Alternatively, the starting material III can be initially introduced in one of the above diluents, after which the starting material II and an acid acceptor are added, either simultaneously or in any desired sequence, through two separate feeds.

In many cases, the reaction is complete immediately after addition of the components; if not, the mixture is stirred further for from 10 minutes to 10 hours at from −50° to 150° C., preferably from 0° to 120° C., in particular from 10° to 50° C., until the reaction is complete.

If an inert gas is used to remove the hydrogen halide, it is advantageous to stir the mixture, after addition of the components, for from 0.2 to 10 hours at from 40° to 100° C.

The end product I is isolated from the reaction mixture in a conventional manner, for example after distilling off the solvent or excess starting material III, or directly, by filtering off under suction. In this case, the residue is washed with water or dilute alkali to remove acidic impurities, and is dried. In the case of water-immiscible diluents, the reaction mixture can also be extracted directly with water or with dilute alkali, and then dried and evaporated down. However, it is also possible to dissolve the residue in a water-immiscible solvent, and wash the solution as described. The desired end products are thereby obtained in a pure form; where appropriate, they can be purified by recrystallization, chromatography or distillation.

The starting compounds of the formula II are obtained by reacting a compound of the formula

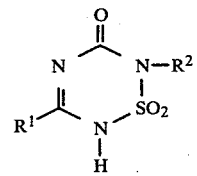

(IV)

where $R^1$ and $R^2$ have the meanings given in claim 1, or its alkali metal salt or alkaline earth metal salt, with an acid halide of phosphoric acid, phosphorus acid, carbonic acid, oxalic acid or sulfurous acid, in the presence or absence of a solvent or diluent and of a reaction accelerator.

Advantageously, the reaction is carried out in a solvent or diluent which is inert under the reaction conditions. Examples of these are halohydrocarbons, in particular chlorohydrocarbons, eg. tetrachloroethylene, 1,1,2,2- and 1,1,1,2-tretrachloroethane, dichloropropane, methylene chloride, dichlorobutane, chloroform, chloronaphthalene, dichloronaphthalene, carbon tetrachloride, 1,1,1- and 1,1,2-tetrachloroethane, trichloroethylene, pentachloroethane, o-, m- and p-difluorobenzene, 1,2-dichloroethane, 1,1-dichloroethane, 1,2-cis-dichloroethylene, chlorobenzene, fluorobenzene, bromobenzene, o-, m- and p-dichlorobenzene, o-, m- and p-dibromobenzene, o-, m- and p-chlorotoluene and 1,2,4-trichlorobenzene, ethers, eg. ethyl propyl ether, methyl tert.-butyl ether, n-butyl ether, diisopropyl ether, anisole, dioxane and ethylene glycol dimethyl ether; nitrohydrocarbons, eg. nitrobenzene, o-, m- and p-chloronitrobenzene and o-nitrotoluene; nitriles, eg. acetonitrile, butyronitrile, isobutyronitrile, benzonitrile and m-chlorobenzonitrile; aliphatic or cycloaliphatic hydrocarbons, eg. heptane, pinane, nonane, o-, m- and p-cymene, gasoline fractions boiling within a range of from 70° to 190° C., cyclohexane, methylcyclohexane, decalin, petroleum ether, hexane, naphtha, 2,2,4-trimethylpentane and 2,2,3-trimethylpentane; and esters, eg. ethyl acetate, and mixtures of the above. Other suitable solvents are inorganic acid chlorides, eg. phosphorus oxychloride, and mixtures of these with inert chlorohydrocarbons, eg. 1,2-dichloroethane. Advantageously, the solvent is used in an amount of from 100 to 2,000, preferably from 200 to 700, % by weight, based on the starting material of the formula IV.

Preferred acid halides are thionyl chloride, sulfur tetrafluoride, phosgene, oxalyl chloride, phosphorus tribromide and, in particular phosphorus pentachloride, phosphorus trichloride and phosphorus oxychloride. The reaction is carried out in general with from 1.0 to 1.5, preferably from 1.05 to 1.2, moles of acid halide per mole of starting material IV; in the case of the phosphorus pentahalide, from 0.7 to 1.5, preferably from 1.0 to 1.2, moles thereof are used per mole of starting material IV.

Where a phosphorus(V) halide is used as the halogenating agent, it is advisable to use a phosphorus oxyhalide as the diluent, preferably in an amount of from 1 to 10 moles per mole of starting material IV.

The phosphorus(V) halide can also be prepared directly in situ, for example by reacting a mixture of a phosphorus(III) halide in the phosphorus oxyhalide, or in one of the above inert solvents, with the requisite stoichiometric amount of active halogen, for example by the method described in U.S. Pat. No. 1,906,440, after which the starting material IV is added and the main reaction is effected.

Advantageous reaction accelerators to use are an N-disubstituted linear or cyclic carboxylic acid amide, a tetraalkyl-substituted urea or a tertiary amine, in amounts of from 1 to 10% by weight, based on starting material IV. Mixtures of the said catalysts may also be used for the reaction. Furthermore, salts of diamines, eg. the amine hydrochloride, or quaternary salts of amines, may be used. Preferred catalysts are triethylamine, pyridine, N,N-dimethylaniline, N-ethylpiperidine, N-methylpyrrolidine, α, β- and γ-picoline, quinoline, isoquinoline, quinazoline, quinoxaline, N-propyldiisopropylamine, 2,6- and 2,4-lutidine, N-(pyrid-4-yl)-pyridinium chloride hydrochloride, p-dimethylaminopyridine, pyrimidine, acridine, dimethylformamide, diethylformamide, N-methylformanilide, N,N-dimethylacetamide, N-methylpyrrolidone and tetramethylurea.

Some of the 2H-1,2,4,6-thiatriazin-3-one-1,1-dioxides required as starting materials of the formula IV are known; both these and the compounds not previously known can be prepared by reacting an N-carboalkoxyamidine with an aminosulfonyl halide.

EXAMPLE 1

2-Ethyl-5-methyl-3-methoxy-2H-1,2,4,6-thiatriazine-1,1-dioxide (No. 1)

225 parts of 2-ethyl-5-methyl-2H-1,2,4,6-thiatriazin-3-one-1,1-dioxide were introduced into a mixture of 1,300 parts of phosphorus oxychloride and 292 parts of phosphorus pentachloride in the course of 2 minutes, while stirring. The reaction mixture was stirred under reflux for 7 hours and then concentrated under reduced pressure. The oil which remained was taken up in 350 parts of 1,2-dichloroethane and chromatographed over neutral alumina (activity I). The solution was then evaporated down, giving 230 parts (93% of theory) of 3-chloro-2-ethyl-5-methyl-2H-1,2,4,6-thiatriazine-1,1-dioxide of melting point 57°–59° C. (NMR (60 MHz, CDCl$_3$): CH$_3$-C 2.3δ, N-CH$_2$ 3.68–4.03δ (q), CH$_3$-C 1.2–1.43δ (t)).

19.8 parts of 30 percent strength sodium methylate were added to a solution of 20.95 parts of 3-chloro-2-ethyl-5-methyl-2H-1,2,4,6-thiatriazine-1,1-dioxide in 120 parts of tetrahydrofuran at 20°–25° C. in the course of 10 minutes, while stirring. The reaction mixture was stirred for three hours at 25° C. and then concentrated, the residue was taken up in ethyl acetate, and the solution was extracted twice with dilute sodium carbonate solution. The organic phase was separated off, dried and chromatographed over silica gel. The solution was then concentrated under reduced pressure, giving 14.5 parts of 2-ethyl-5-methyl-3-methoxy-2H-1,2,4,6-thiatriazine-1,1-dioxide of melting point 50°–53° C.

EXAMPLE 2

2,5-Dimethyl-3-(4'-nitrophenoxy)-2H-1,2,4,6-thiatriazine-1,1-dioxide (No. 2)

212 parts of 2,5-dimethyl-2H-1,2,4,6-thiatriazin-3-one-1,1-dioxide were introduced into a mixture of 292 parts of phosphorus pentachloride and 1,400 parts of phosphorus oxychloride at room temperature, while stirring. The reaction mixture was heated to 110° C. in the course of 30 minutes, stirred under reflux for 6 hours, and then concentrated under reduced pressure, giving 234 parts (100% of theory) of 3-chloro-2,5-dimethyl-2H-1,2,4,6-thiatriazine-1,1-dioxide of melting point 86°–90° C. (NMR (60 MHz, CDCl$_3$): CH$_3$-C 2.4δ, CH$_3$-N 3.68δ).

12.8 parts of p-nitrophenol in 30 parts of acetone and 9.3 parts of triethylamine were introduced in the course of 15 minutes, through two separate feeds, into a stirred solution of 18 parts of 3-chloro-2,5-dimethyl-2H-1,2,4,6-thiatriazine-1,1-dioxide in 150 parts of acetone, at 20°–25° C. The reaction mixture was stirred for one hour at room temperature, after which the precipitate was filtered off under suction, the filtrate was concentrated under reduced pressure and the residue was taken up in methylene chloride. The solution was extracted twice with 0.5 N sodium hydroxide solution, dried over magnesium sulfate, chromatographed over neutral alumina and concentrated under reduced pressure, giving 18.5 parts of 2,5-dimethyl-3-p-nitrophenoxy-2H-1,2,4,6-thiatriazine-1,1-dioxide of melting point 194°–197° C.

EXAMPLE 3

2,5-Dimethyl-3-m-methoxycarbamylphenoxy-2H-1,2,4,6-thiatriazine-1,1-dioxide (No. 3)

18.4 parts of m-hydroxyphenyl N-methylcarbamate and 11.1 parts of triethylamine were added to a stirred solution of 19.5 parts of 3-chloro-2,5-dimethyl-2H-1,2,4,6-thiatriazine-1,1-dioxide in 140 parts of ethyl acetate in the course of 10 minutes, at 25°–30° C. The reaction mixture was stirred for 5 hours at room temperature, after which the precipitate was filtered off under suction and the filtrate was extracted with dilute sodium carbon solution. The organic phase was dried and evaporated down, giving 21.8 parts of colorless 2,5-dimethyl-3-m-methoxycarbamylphenoxy-2H-1,2,4,6-thiatriazine-1,1-dioxide of melting point 181°–184° C.

EXAMPLE 4

2,5-Dimethyl-3-p-(α-methoxycarbonyl-ethoxy)-phenoxy-2H-1,2,4,6-thiatriazine-1,1-dioxide (No. 205)

19.6 parts of 3-chloro-2,5-dimethyl-2H-1,2,4,6-thiatriazine-1,1-dioxide in 60 parts of ethyl acetate, 19.6 parts of methyl α-(p-hydroxyphenoxy)-propionate in 60 parts of ethyl acetate and 7.9 parts of pyridine were introduced separately, in the course of 10 minutes, into 140 parts of ethyl acetate, at 0°–10° C., while stirring. The reaction mixture was stirred for one hour at room temperature, after which the precipitate was filtered off under suction and the filtrate was extracted once with 0.5 N hydrochloric acid and twice with dilute sodium carbonate solution. The organic phase was dried, chromatographed over neutral alumina and concentrated under reduced pressure, giving 21 parts of 2,5-dimethyl-3-p-(α-methoxycarbonyl-ethoxy)-phenoxy-2H-1,2,4,6-thiatriazine-1,1-dioxide of melting point 106°–109° C.

The following 2H-1,2,4,6-thiatriazine-1,1-dioxides of the formula I were obtained analogously:

| Compound no. | $R^1$ | Y | $R^2$ | $R^3$ | M.p.[°C.]/$n_D^{25}$ |
|---|---|---|---|---|---|
| 5 | $CH_3$ | O | $CH_3$ | $CH_3$ | 97–100 |
| 6 | $CH_3$ | O | $C_2H_5$ | $CH_3$ | 1.4990 |
| 14 | $C_2H_5$ | O | $CH_3$ | $CH_3$ | 83–84 |
| 18 | $C_2H_5$ | O | 1-propyn-3-yl | $CH_3$ | 78–80 |
| 19 | $C_2H_5$ | O | $CH_2$—$CH$=$CH_2$ | $CH_3$ | 1.5018 |
| 20 | $C_2H_5$ | O | 4-methylbenzyl | $CH_3$ | 87–91 |
| 30 | $CH_3$ | O | $CH_2$—CO—$CH_3$ | $CH_3$ | 1.5092 |
| 35 | $CH_3$ | O | 2-(3-chlorophenoxy)-ethyl | $CH_3$ | 112–116 |
| 36 | $CH_3$ | O | $CH(CH_3)CO_2C_2H_5$ | $CH_3$ | 70–73 |
| 45 | i-$C_3H_7$ | O | prop-2-ynyl | $CH_3$ | 1.5060 |
| 47 | $CH_3$ | O | $CH_2$—CH=CH—$CH_3$ | $CH_3$ | 1.4891 |
| 51 | $CH_3$ | O | $CH_2$—CH=$CH_2$ | $CH_3$ | 1.5124 |
| 58 | $CH_3$ | O | i-$C_3H_7$ | $CH_3$ | 1.4819 |
| 63 | $CH_3$ | O | 3-methoxybenzyl | $CH_3$ | 82–85 |
| 82 | $CH_3$ | O | 4-methylbenzyl | $CH_3$ | 82–84 |
| 84 | $C_2H_5$ | O | 3-methoxybenzyl | $CH_3$ | 82–84 |
| 90 | $CH_3$ | O | prop-1-yn-3-yl | $CH_3$ | 56–60 |
| 98 | i-$C_4H_9$ | O | prop-1-yn-3-yl | $CH_3$ | 1.5030 |
| 109 | $CH_3$ | O | 2,4-dinitro-6-sec.-butylphenyl | $CH_3$ | 128–133 |
| 112 | $CH_3$ | O | 2,6-dibromo-4-cyanophenyl | $CH_3$ | 179–182 |
| 115 | $CH_3$ | O | 4-trifluoromethylbenzyl | $CH_3$ | 115–117 |
| 125 | $CH_3$ | O | 4-nitrophenyl | $C_2H_5$ | 196–198 |
| 130 | $CH_3$ | O | 4-chlorobenzyl | $CH_3$ | 86–90 |
| 140 | i-$C_4H_9$ | O | $CH_3$ | $CH_3$ | 1.4935 |
| 144 | $CH_3$ | O | 3,4-dichlorobenzyl | $CH_3$ | 148–150 |
| 145 | $C_2H_5$ | O | 4-nitrophenyl | $CH_3$ | 146–148 |
| 153 | i-$C_3H_7$ | O | $CH_3$ | $CH_3$ | 1.4942 |
| 154 | $CH_3$ | O | benzyl | $CH_3$ | 121–124 |
| 158 | $CH_3$ | O | 1-propyn-3-yl | $C_2H_5$ | 1.5121 |
| 160 | $C_2H_5$ | O | benzyl | $CH_3$ | 88–90 |
| 161 | $CH_3$ | O | 2,6-dichlorobenzyl | $CH_3$ | 127–130 |
| 162 | n-$C_3H_7$ | O | $CH_2$—CH=$CH_2$ | $CH_3$ | 1.5028 |
| 163 | n-$C_3H_7$ | O | 1-propyn-3-yl | $CH_3$ | 1.5100 |
| 166 | $CH_3$ | O | benzyl | $C_2H_5$ | 115–118 |
| 167 | $CH_3$ | O | 2-chlorobenzyl | $CH_3$ | 91–95 |
| 173 | $CH_3$ | O | 3-chlorobenzyl | $CH_3$ | 89–92 |
| 177 | $CH_3$ | O | 2-methyl-prop-1-en-3-yl | $CH_3$ | 1.5051 |
| 178 | i-$C_3H_7$ | O | 4-nitrophenyl | $CH_3$ | 159–163 |
| 181 | i-$C_4H_9$ | O | 3-methoxybenzyl | $CH_3$ | 90–94 |
| 185 | $CH_3$ | O | 3-methoxybenzyl | $C_2H_5$ | 82–85 |
| 186 | $CH_3$ | O | $CH_2$—$CCl_3$ | $CH_3$ | 71–75 |
| 187 | $CH_3$ | O | $ClCH_2$—$(CH_2)_2$— | $CH_3$ | 1.5080 |
| 190 | $N(CH_3)_2$ | O | $CH_3$ | $CH_3$ | 159–162 |
| 191 | $N(CH_3)_2$ | O | benzyl | $CH_3$ | 114–118 |
| 192 | $N(CH_3)_2$ | O | 4-nitrophenyl | $CH_3$ | 202–204 |
| 199 | $N(C_2H_5)_2$ | O | $CH_2$—C≡CH | $CH_3$ | 58–62 |
| 200 | $CH_3$ | O | 2,4-dichlorobenzyl | $CH_3$ | 117–118 |
| 201 | $CH_3$ | O | $(CH_2)_4CH_3$ | $CH_3$ | 1.4860 |

The following 2H-1,2,4,6-thiatriazine-1,1-dioxides of the formula I may be obtained analogously:

| Compound no. | $R^1$ | Y | $R^2$ | $R^3$ | M.p.[°C.]/$n_D^{25}$ |
|---|---|---|---|---|---|
| 4 | $CH_3$ | O | $CH_3$ | H | |
| 7 | $CH_3$ | O | $C_2H_5$ | $C_2H_5$ | |
| 8 | $CH_3$ | O | $C_2H_5$ | i-$C_3H_7$ | |
| 9 | $CH_3$ | O | $CH_2$—CH=$CH_2$ | $C_2H_5$ | |
| 10 | $CH_3$ | S | $CH_3$ | $CH_3$ | |
| 11 | $CH_3$ | S | $CH_2$—CH=$CH_2$ | $CH_3$ | |
| 12 | $CH_3$ | $SO_2$ | $CH_3$ | $CH_3$ | |
| 13 | $CH_3$ | O | $CH_2$—CH=$CH_2$ | H | |
| 15 | $C_2H_5$ | O | $C_2H_5$ | $CH_3$ | |
| 16 | $C_2H_5$ | O | $C_2H_5$ | $C_2H_5$ | |
| 17 | $C_2H_5$ | O | $CH_2$—CH=$CH_2$ | $C_2H_5$ | |
| 21 | $C_2H_5$ | O | CH=CH—$CH_2Cl$ | $CH_3$ | |
| 22 | $C_2H_5$ | O | CH=CCl—$CH_3$ | $CH_3$ | |
| 23 | n-$C_3H_7$ | O | $CH_2$—$CH_2$—O—$CH_3$ | $CH_3$ | |
| 24 | n-$C_3H_7$ | O | 1-chloro-2-butyn-4-yl | $CH_3$ | |
| 25 | i-$C_3H_7$ | O | 1-methoxy-2-butyn-4-yl | $C_2H_5$ | |
| 26 | $CH_3$ | O | 1-methylmercapto-but-2-yn-4-yl | $CH_3$ | |
| 27 | n-$C_3H_7$ | O | 1-chloro-but-3-yn-2-yl | $C_2H_5$ | |
| 28 | $CH_3$ | S | $CH_2$—CCl=$CH_2$ | $CH_3$ | |
| 29 | $C_2H_5$ | O | $CH_2$—CH=CH—CO—$CH_3$ | $CH_3$ | |
| 31 | $CH_3$ | O | $CH_2$—$CH_2$—S—$CH_3$ | $CH_3$ | |
| 32 | i-$C_3H_7$ | O | $CH_3$ | $CH_3$ | |
| 33 | n-$C_4H_5$ | | $CH_3$ | | |

-continued

| Compound no. | R¹ | Y | R² | R³ | M.p.[°C.]/$n_D^{25}$ |
|---|---|---|---|---|---|
| 34 | sec-C₄H₉ | O | n-C₃H₇ | CH₃ | |
| 37 | CH₃ | O | 4-trifluoromethylphenyl | CH₃ | |
| 38 | CH₃ | O | 3-difluoromethoxyphenyl | CH₃ | |
| 39 | CH₃ | S | 3-chlorophenyl | CH₃ | |
| 40 | CH₃ | O | n-C₃H₇ | CH₃ | |
| 41 | C₂H₅ | O | n-C₄H₉ | C₂H₅ | |
| 42 | CH₃ | O | 4-methylmercaptophenyl | C₂H₅ | |
| 43 | CH₃ | O | 4-methoxyphenyl | CH₃ | |
| 44 | CH₃ | O | CH₃ | C₂H₅ | |
| 46 | n-C₄H₉ | O | C₂H₅ | C₂H₅ | |
| 48 | CH₃ | O | 2-butyn-4-yl | CH₃ | |
| 49 | CH₃ | O | but-1-yn-3-yl | CH₃ | |
| 50 | C₂H₅ | O | but-1-yn-3-yl | CH₃ | |
| 52 | i-C₃H₇ | O | CH₂—CO—CH₃ | CH₃ | |
| 53 | CH₂—CH=CH₂ | O | CH₃ | CH₃ | |
| 54 | propargyl | O | CH₃ | C₂H₅ | |
| 55 | CH₂—CH₂—Cl | O | C₂H₅ | CH₃ | |
| 56 | cyclohexyl | O | CH₃ | i-C₃H₇ | |
| 57 | 3-chlorophenyl | O | CH₃ | CH₃ | |
| 59 | C₂H₅ | S | n-C₄H₉ | C₂H₅ | |
| 60 | n-C₃H₇ | O | C₂H₅ | CH₃ | |
| 61 | CH₃ | O | 4-methylphenyl | C₂H₅ | |
| 62 | CH₃ | O | 4-trifluoromethyl-mercaptophenyl | CH₃ | |
| 64 | C₂H₅ | O | C₂H₅ | i-C₃H₇ | |
| 65 | tert-C₄H₉ | O | CH₃ | CH₃ | |
| 66 | C₂H₅ | O | CH₃ | i-C₃H₇ | |
| 67 | C₂H₅ | SO₂ | CH₃ | CH₃ | |
| 68 | CH₃—O—CH₂CH₂ | O | CH₃ | CH₃ | |
| 69 | C₂H₅ | O | C₂H₅ | CH₃ | |
| 70 | C₆H₅—CH₂ | O | CH₃ | CH₃ | |
| 71 | 4-chlorobenzyl | O | CH₃ | CH₃ | |
| 72 | 4-methoxyphenyl | O | C₂H₅ | CH₃ | |
| 73 | i-C₃H₇ | O | CH₃ | n-C₃H₇ | |
| 74 | CH₃ | S | prop-1-yn-3-yl | CH₃ | |
| 75 | CH₃ | O | CH₃ | i-C₃H₇ | |
| 76 | CH₃ | O | CH₃ | sec.-C₄H₉ | |
| 77 | CH₃ | O | C₂H₅ | tert.-C₄H₉ | |
| 78 | CH₃ | O | 1-propyn-3-yl | H | |
| 79 | C₂H₅ | O | CH₂—CH=CH—$\overset{O}{\overset{\|}{C}}$—CH₃ | C₂H₅ | |
| 80 | CH₃—S—CH₂—CH₂ | O | CH₃ | CH₃ | |
| 81 | CH₃ | O | CH₂—CH=CH₂ | CH₂—CH=CH₂ | |
| 83 | CH₃ | O | CH₃ | cyclohexyl | |
| 85 | CH₃ | O | CH₃ | CH₂—O—CH₃ | |
| 86 | CH₃ | O | CH₃ | CH₂—CH₂—Cl | |
| 87 | C₂H₅ | O | CH₃ | CH₂—CH₂—F | |
| 88 | CH₃ | O | 4-nitrophenyl | CH₃ | |
| 89 | CH₃ | O | 4-methylsulfinyl-phenyl | CH₃ | |
| 91 | CH₃ | O | 4-cyanophenyl | CH₃ | |
| 92 | CH₃ | O | 4-thiocyanatophenyl | CH₃ | |
| 93 | i-C₃H₇ | O | 3-carboxyphenyl | CH₃ | |
| 94 | CH₃ | O | 4-nitro-3-carboxyphenyl | CH₃ | |
| 95 | CH₃ | O | 2-methyl-4,6-dinitrophenyl | CH₃ | |
| 96 | C₂H₅ | S | 4-nitrophenyl | CH₃ | |
| 97 | n-C₃H₇ | O | 4-methylsulfonylphenyl | CH₃ | |
| 99 | CH₃ | O | 3,5-dichlorophenyl | C₂H₅ | |
| 100 | CH₃ | O | 2,5-dichlorophenyl | n-C₃H₇ | |
| 101 | CH₃ | S | 4-methoxycarbonylphenyl | CH₃ | |
| 102 | CH₃ | O | 2,4,6-trichlorophenyl | CH₃ | |
| 103 | CH₃ | O | 4-methylmercapto-carbonyl-phenyl | C₂H₅ | |
| 104 | C₂H₅ | O | 4-(N—methylcarbamoyl)-phenyl | C₂H₅ | |
| 105 | CH₃ | O | 4-(N,N—dimethylcarbamoyl)-phenyl | CH₃ | |
| 106 | CH₃ | O | 2,4-dinitro-6-tert.-butyl-phenyl | CH₃ | |
| 107 | CH₂=CH—CH₂ | O | 3-methoxycarbonylamino-phenyl | C₂H₅ | |
| 108 | i-C₃H₇ | O | 4-methoxycarbonylamino-phenyl | CH₃ | |
| 110 | n-C₃H₇ | O | 4-methylmercaptocarbonyl-aminophenyl | CH₃ | |
| 111 | CH₃ | O | 4-(N—methylsulfamoyl-amino)-phenyl | CH₃ | |
| 113 | C₂H₅ | O | 4-(N,N—dimethylsulfamoyl-amino)-phenyl | C₂H₅ | |
| 114 | CH₃ | O | 4-formylphenyl | C₂H₅ | |
| 116 | CH₃ | O | 2,6-diiodo-4-cyanophenyl | CH₃ | |

-continued

| Compound no. | R¹ | Y | R² | R³ | M.p.[°C.]/$n_D^{25}$ |
|---|---|---|---|---|---|
| 117 | CH₃ | O | 2-nitrophenyl | C₂H₅ | |
| 118 | CH₃ | O | 3-nitrophenyl | CH₃ | |
| 119 | C₂H₅ | O | 4-(N—hydroxyiminomethyl)-phenyl | CH₃ | |
| 120 | CH₃ | O | 3-methylsulfonyl-phenyl | CH₃ | |
| 121 | C₂H₅ | O | 4-(N,N—dimethylsulfamoyl-phenyl | CH₃ | |
| 122 | CH₃ | O | 4-chlorophenyl | CH₃ | |
| 123 | CH₃ | O | 3-carboxymethoxyphenyl | i-C₃H₇ | |
| 124 | C₂H₅ | O | 3-methoxycarbonyl-methoxy-phenyl | CH₃ | |
| 126 | CH₃ | O | 4-methoxycarbonylmethyl-mercapto-phenyl | CH₃ | |
| 127 | C₂H₅ | O | 3-methylmercaptocarbonyl-methylmercapto-phenyl | CH₃ | |
| 128 | CH₃ | O | 4-tert.-butylphenyl | CH₃ | |
| 129 | C₂H₅ | S | 2,6-dimethylphenyl | CH₃ | |
| 131 | CH₃ | O | 4-cyanophenyl | CH₃ | |
| 132 | CH₃ | O | 3,4-difluorophenyl | CH₃ | |
| 133 | CH₃ | O | 3-tert.-butylphenyl | CH₃ | |
| 134 | C₂H₅ | O | 4-tert.-butylphenyl | CH₃ | |
| 135 | CH₃ | O | 2,4-dichloro-6-methylphenyl | CH₃ | |
| 136 | C₂H₅ | O | 2-chloro-4-nitrophenyl | CH₃ | |
| 137 | CH₃ | O | 4-nitrophenyl | H | |
| 138 | CH₃ | O | 4-trifluoromethyl-2-chlorophenyl | CH₃ | |
| 139 | CH₃ | O | 3-chloro-4-methoxyphenyl | H | |
| 141 | CH₃ | O | 3-methoxycarbonylamino-phenyl | CH₃ | |
| 142 | CH₃ | O | 3-methylaminocarbonyl-aminophenyl | CH₃ | |
| 143 | C₂H₅ | O | 4-(1-methoxycarbonyl)-ethoxyphenyl | CH₃ | |
| 146 | i-C₃H₇ | O | 2-chloro-4-nitrophenyl | CH₃ | |
| 147 | C₂H₅ | O | 4-nitrophenyl | i-C₃H₇ | |
| 148 | CH₃ | O | 4-nitro-3-methoxycarbonyl-phenyl | CH₃ | |
| 149 | sec.-C₄H₉ | O | 4-nitrophenyl | i-C₃H₇ | |
| 150 | C₂H₅ | S | benzyl | CH₃ | |
| 151 | CH₃ | O | 4-nitrophenyl | i-C₃H₇ | |
| 152 | CH₃ | O | 4-nitrophenyl | n-C₃H₇ | |
| 155 | CH₃ | O | 3-trifluoromethoxy-phenyl | CH₃ | |
| 156 | CH₃ | O | sec.-butyl | CH₃ | |
| 157 | C₂H₅ | S | 1-propyn-3-yl | CH₃ | |
| 159 | C₂H₅ | O | 1-propyn-3-yl | C₂H₅ | |
| 164 | C₂H₅ | O | 2,6-dichlorobenzyl | CH₃ | |
| 165 | C₂H₅ | S | allyl | CH₃ | |
| 168 | C₂H₅ | O | 2-chlorobenzyl | CH₃ | |
| 169 | CH₃ | O | 2-chlorobenzyl | C₂H₅ | |
| 170 | CH₃ | O | 2,6-dichlorobenzyl | C₂H₅ | |
| 171 | C₂H₅ | O | benzyl | C₂H₅ | |
| 172 | C₂H₅ | O | 4-nitrophenyl | C₂H₅ | |
| 174 | C₂H₅ | O | 3-chlorobenzyl | C₂H₅ | |
| 175 | CH₃ | O | 3-chlorobenzyl | CH₃ | |
| 176 | CH₃ | S | CH₂—CH=CH₂ | CH₃ | |
| 179 | CH₃ | O | 3,4-dichlorobenzyl | CH₃ | |
| 180 | CH₃ | O | 3,4-dichlorobenzyl | C₂H₅ | |
| 182 | C₂H₅ | O | 3-trifluoromethyl-phenyl | H | |
| 183 | C₂H₅ | O | 2-fluoro-6-chlorobenzyl | CH₃ | |
| 184 | CH₃ | O | 4-chlorobenzyl | C₂H₅ | |
| 188 | N(CH₃)₂ | O | allyl | CH₃ | |
| 189 | N(CH₃)₂ | O | prop-1-yn-3-yl | CH₃ | |
| 193 | CH₃ | O | cyclopentyl | CH₃ | |
| 194 | CH₃ | O | cyclohexyl | CH₃ | |
| 195 | CH₃ | O | methoxycarbonylmethyl | CH₃ | |
| 196 | CH₃ | O | methylmercaptocarbonyl-methyl | CH₃ | |
| 197 | CH₃ | O | 2-(2,4-dichlorophenoxy)-ethyl | CH₃ | |
| 198 | CH₃ | O | 2-(3-methoxyphenoxy)-ethyl | CH₃ | |
| 202 | CH₃ | O | CH₂—CH₂—O—CH₃ | CH₃ | |
| 203 | CH₃ | O | CH₂—CH₂—O—C₂H₅ | CH₃ | |
| 204 | CH₃ | O | CH₂—CH=C(CH₃)₂ | CH₃ | |

The compounds of the formula I may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 90 parts by weight of the compound of Example 1 is mixed with 10 parts by weight of N-methyl-alpha-pyrrolidone. A mixture is obtained which is suitable for application in the form of very fine drops.

II. 20 parts by weight of the compound of Example 2 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of the compound of Example 3 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of the compound of Example 4 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 35 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 13 is intimately mixed with 97 parts by weight of particulate kaolin. A dust is obtained containing 3% by weight of the active ingredient.

VII. 30 parts by weight of compound no. 36 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 1 is intimately mixed with 46 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients, or formulations containing them, may be applied pre- or postemergence. The agents may be applied before the unwanted plants have germinated from seed or sprouted from vegetative plant parts, or they may be applied to the leaves of unwanted and crop plants. Preferably, the novel active ingredients are applied during or after emergence of the unwanted plants, both on cropland and uncropped land. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient depends on the time of the year and the growth stage of the plants, and varies from 0.1 to 15 kg/ha and more, but is preferably from 0.5 to 4 kg/ha. The higher application rates are particularly suitable for total elimination of vegetation.

The herbicidal action of compounds of the formula I is demonstrated in greenhouse experiments.

The vessels employed were plastic flowerpots having a volume of 300 cm$^3$, and which were filled with a sandy loam containing about 1.5% humus. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. After the agents had been applied, the vessels were lightly sprinkler-irrigated to induce germination and growth and to activate the chemical agents. Transparent plastic covers were then placed on the vessels until the plants had taken root. The cover ensured uniform germination of the plants, insofar as this was not impaired by the chemicals.

For the postemergence treatment, the plants were first grown in the vessels to a height of from 3 to 15 cm, depending on growth form, before being treated. For this treatment, either plants which has been sown directly in the pots and grown there were selected, or plants which had been grown separately as seedlings and transplanted to the experiment vessels.

No cover was placed on the vessels in the postemergence treatment. The pots were set up in the greenhouse - species from warmer areas at from 20° to 30° C., and species from moderate climates at 15° to 25° C. The experiments were run for from 3 to 5 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The plants employed for the experiments were Amaranthus spp., *Chenopodium album*, Chrysanthemum spp., *Datura stramonium, Galium aparine, Gossypium hirsutum*, Matricaria spp., *Nicandra physaloides, Oryza sativa, Sesbania exaltata, Sinapis alba, Solanum nigrum, Triticum aestivum, Zea mays, Lolium multiflorum*, Ipomoea spp., *Cyperus esculentus*, and *Centaurea cyanus.*

The experiments showed that for instance compounds nos. 2, 51, 109 and 154, applied preemergence at a rate of 2.0 kg/ha, had a good herbicidal action, and some crop plants remained substantially unaffected. Compound no. 186, at a low application rate, controlled broadleaved weeds in Indian corn, and compound no. 47 controlled unwanted plant growth in rice.

A fairly small amount of compound no. 112, applied post-emergence, combatted a number of unwanted plants. Compounds nos. 179 and 187 had a good herbicidal action on both pre- and post-emergence application.

In view of the good tolerance of the active ingredients and the many application methods possible, the compounds according to the invention, or agents containing them, can be used—in addition to the crop plants employed in the experiments—in a further, large number of crops for removing unwanted plant growth.

The following crops may be mentioned by way of example:

| Botanical name | Common name |
|---|---|
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. altissima | sugarbeets |
| *Beta vulgaris* spp. rapa | fodder beets |
| *Beta vulgaris* spp. esculenta | table beets, red beets |
| *Brassica napus* var. napus | rape |
| *Brassica napus* var. napobrassica | |
| *Brassica napus* var. rapa | turnips |
| *Brassica rapa* var. silvestris | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica (Coffea canephora, Coffea liberica)* | coffee plants |
| *Cucumis melo* | melons |
| *Cucumis sativus* | cucumbers |
| *Cynodon dactylon* | Bermudagrass in turf and lawns |
| *Daucus carota* | carrots |
| *Elais guineensis* | oil palms |
| *Fragaria vesca* | strawberries |
| *Glycine max* | soybeans |
| *Gossypium hirsutum (Gossypium arboreum Gossypium herbaceum Gossypium vitifolium)* | cotton |
| *Helianthus annuus* | sunflowers |
| *Helianthus tuberosus* | |
| *Hevea brasiliensis* | rubber plants |
| *Hordeum vulgare* | barley |
| *Humulus lupulus* | hops |
| *Ipomoea batatas* | sweet potatoes |
| *Juglans regina* | walnut trees |
| *Lactuca sativa* | lettuce |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Mentha piperita* | peppermint |
| *Musa* spp. | banana plants |
| *Nicothiana tabacum (N. rustica)* | tobacco |
| *Olea europaea* | olive trees |
| *Oryza sativa* | rice |
| *Panicum miliaceum* | |
| *Phaseolus lunatus* | limabeans |
| *Phaselous mungo* | mungbeans |
| *Phaseolus vulgaris* | snapbeans, green beans, dry beans |
| *Pennisetum glaucum* | |
| *Petroselium crispum* spp. tuberosum | parsley |
| *Picea abies* | Norway spruce |
| *Abies alba* | fir trees |
| *Pinus* spp. | pine trees |
| *Pisum sativum* | English peas |
| *Prunus avium* | cherry trees |
| *Prunus domestica* | plum trees |
| *Prunus dulcis* | almond trees |
| *Purnus persica* | peach trees |
| *Pyrus communis* | pear trees |
| *Ribes sylvestre* | red currants |
| *Ribes uva-crispa* | gooseberries |
| *Ricinus communis* | castor-oil plants |
| *Saccharum officinarum* | sugar cane |

| Botanical name | Common name |
| --- | --- |
| *Secale cereale* | rye |
| *Sesamum indicum* | sesame |
| *Solanum tuberosum* | Irish potatoes |
| *Sorghum bicolor* (s. vulgare) | sorghum |
| *Sorghum dochna* | |
| *Spinacia oleracea* | spinach |
| *Theobroma cacao* | cacao plants |
| *Trifolium pratense* | red clover |
| *Triticum aestivum* | wheat |
| *Vaccinium corymbosum* | blueberries |
| *Vaccinium vitis-idaea* | cranberries |
| *Vicia faba* | tick beans |
| *Vigna sinensis* (V. unguiculata) | cow peas |
| *Vitis vinifera* | grapes |
| *Zea mays* | Indian corn, sweet corn, maize |

To increase the spectrum of action and to achieve synergistic effects, the novel compounds according to the invention may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, etc.

It may also be useful to apply the novel compounds, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. To initiate the herbicidal action, wetting agents, spreader-stickers, and non-phytotoxic oils and oil concentrates may be also added.

We claim:

1. A 2H-1,2,4,6-thiatriazine-1,1-dioxide of the formula

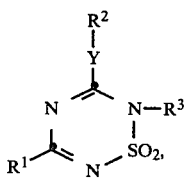 (I)

where $R_1$ is hydrogen, a saturated or unsaturated straight-chain or branched aliphatic radical of not more than 10 carbon atoms, a saturated straight-chain or branched aliphatic radical of not more than 10 carbon atoms which is substituted by halogen, alkoxy or alkylmercapto of 1 to 4 carbon atoms, an alkyl or dialkylamino radical where alkyl is of 1 to 6 carbon atoms, cycloalkyl of 3 to 7 carbon atoms, phenyl which is unsubstituted or substituted by halogen, alkyl or alkoxy of 1 to 4 carbon atoms, or benzyl which is unsubstituted or substituted by halogen, $R^2$ is a saturated or unsaturated straight-chain or branched aliphatic radical of not more than 10 carbon atoms, a saturated or unsaturated straight-chain or branched aliphatic radical of not more than 10 carbon atoms which is substituted by halogen, alkoxy or alkylmercapto of 1 to 4 carbon atoms or alkanoyl of 2 to 8 carbon atoms, cycloalkyl of 3 to 7 carbon atoms, alkoxycarbonylalkyl or alkylmercaptocarbonylalkyl where each alkyl is of 1 to 4 carbon atoms, phenyl which is unsubstituted or substituted by halogen, an alkyl, haloalkyl, alkoxy, haloalkoxy, alkylmercapto, haloalkylmercapto, alkylsulfinyl, haloalkylsulfinyl, alkylsulfonyl or haloalkylsulfonyl radical of 1 to 4 carbon atoms, nitro, cyano, azido, carboxyl, thiocyanato, hydroxyiminomethyl, formyl, an alkoxycarbonyl or alkylmercaptocarbonyl radical of 2 to 5 carbon atoms, an N-alkylcarbamyl, N,N-dialkylcarbamyl, N-alkylcarbamylamino or N,N-dialkylcarbamylamino radical where alkyl is of 1 to 4 carbon atoms, 4-alkyl-1,2,4-oxadiazolidine-3,5-dion-2-yl, an alkanoylamino, alkoxycarbonylamino or alkylmercaptocarbonylamino radical of 2 to 5 carbon atoms, an N-alkylsulfamyl, N,N-dialkylsulfamyl, N-alkylsulfamylamino or N,N-dialkylsulfamylamino radical where alkyl is of 1 to 4 carbon atoms, alkoxysulfonyl of 1 to 4 carbon atoms, alkoxycarbonylaminosulfonyl of 2 to 5 carbon atoms or an alkoxycarbonylalkoxy, alkylmercaptocarbonylalkoxy, alkoxycarbonylalkylmercapto or alkylmercaptocarbonylalkylmercapto radical where each alkyl is of 1 to 4 carbon atoms, or $R^2$ is benzyl which is unsubstituted or substituted by halogen, nitro or an alkyl, haloalkyl, alkoxy, haloalkoxy or haloalkylmercapto radical of 1 to 4 carbon atoms, or phenoxyalkyl where alkyl is of 2 to 4 carbon atoms, which is unsubstituted or substituted in the phenyl ring by halogen or by alkyl, alkoxy, haloalkyl, haloalkoxy or haloalkylmercapto of 1 to 4 carbon atoms, $R^3$ is hydrogen, a saturated or unsaturated straight-chain or branched aliphatic radical of not more than 10 carbon atoms, or a saturated straight-chain or branched aliphatic radical of not more than 10 carbon atoms which is substituted by halogen or by alkoxy of 1 to 4 carbon atoms, or is cycloalkyl of 3 to 7 carbon atoms, and Y is oxygen, sulfur, —SO— or —SO$_2$—, 2. A 2H-1,2,4,6-thiatriazine-1,1-dioxide of the formula I as claimed in claim 1, where $R^1$ and $R^3$ are alkyl of 1 to 4 carbon atoms, $R^2$ is an unsaturated aliphatic radical of 3 or 4 carbon atoms, and Y is oxygen or sulfur.

3. A 2H-1,2,4,6-thiatriazine-1,1-dioxide of the formula I as claimed in claim 1, where $R^1$ and $R^3$ are alkyl of 1 to 4 carbon atoms, $R^2$ is phenyl substituted by halogen, nitro, cyano or alkyl of 1 to 4 carbon atoms, and Y is oxygen or sulfur.

4. A 2H-1,2,4,6-thiatriazine-1,1-dioxide of the formula I as claimed in claim 1, where $R^1$ and $R^3$ are alkyl of 1 to 4 carbon atoms, $R^2$ is benzyl which is unsubstituted or substituted by halogen, or by alkyl, alkoxy or haloalkoxy of 1 to 4 carbon atoms, and Y is oxygen or sulfur.

5. 2,5-Dimethyl-3-allyloxy-2H-1,2,4,6-thiatriazine-1,1-dioxide.

6. 2,5-Dimethyl-3-(4'-nitrophenoxy)-2H-1,2,4,6-thiatriazine-1,1-dioxide.

7. A herbicide containing inert additives and a 2H-1,2,4,6-thiatriazine-1,1-dioxide of the formula I as claimed in claim 1.

8. A herbicide as claimed in claim 7, where $R^1$ and $R^3$ are alkyl of 1 to 4 carbon atoms, $R^2$ is an unsaturated aliphatic radical of 3 or 4 carbon atoms, and Y is oxygen or sulfur.

9. A herbicide as claimed in claim 7, where $R^1$ and $R^3$ are alkyl of 1 to 4 carbon atoms, $R^2$ is phenyl substituted by halogen, nitro, cyano or alkyl of 1 to 4 carbon atoms, and Y is oxygen or sulfur.

10. A process for combating the growth of unwanted plants, wherein the plants and/or their location are treated with a herbicidally effective amount of a 2H-1,2,4,6-thiatriazine-1,1-dioxide of the formula I as claimed in claim 1.

* * * * *